United States Patent [19]

Rostoker

[11] Patent Number: 5,514,150
[45] Date of Patent: May 7, 1996

[54] MICROMACHINED CONVEYOR DEVICES

[75] Inventor: Michael D. Rostoker, Boulder Creek, Calif.

[73] Assignee: LSI Logic Corporation, Milpitas, Calif.

[21] Appl. No.: 205,661

[22] Filed: Mar. 3, 1994

[51] Int. Cl.[6] .................................................. A61B 17/00
[52] U.S. Cl. .............................. 606/159; 606/128; 604/22
[58] Field of Search .................................... 606/159, 170, 606/171, 169, 128; 604/22; 433/119; 128/898

[56] References Cited

U.S. PATENT DOCUMENTS

| | | | |
|---|---|---|---|
| 3,565,062 | 2/1971 | Kuris | 606/159 |
| 4,808,156 | 2/1989 | Parisi | 606/159 |

OTHER PUBLICATIONS

"What's Next?Nanotechnology For Manufacturing", by Walker, Microtimes, Oct. 1992, pp. 116, 124, 125, 128, 286, 288.
"Silicon is becoming both bricks and mortar for armies of gears, valves, pumps and sensing devices that may turn the surface of microchips into diminutive factories and laboratories.", Scientific American, Nov. 1992, pp. 107–117.

*Primary Examiner*—Stephen C. Pellegrino
*Assistant Examiner*—William W. Lewis
*Attorney, Agent, or Firm*—Katz & Cotton

[57] ABSTRACT

Various forms of micromachined electrostatic microconveyors and useful devices based thereon are described. In one embodiment, a tube shaped conveyor is formed by disposing conductors circumferentially about the exterior surface of the tube. The tube is formed of an insulating material (e.g., silicon dioxide). Driving voltages are applied in staggered phase to selected ones of the conductors to provide a travelling electrostatic wave within the tube. Charged particles (or fluid or gas) can be propelled through the tube electrostatically by "riding" the travelling wave. Various aspects of the invention are directed to apparatus making use of the microconveyor to convey particles, gas ions, etc.. Apparatus is described for using gas pressure resulting from the transport of gas ions to do mechanical work (i.e., to operate mechanical actuators. A planar microconveyor, similar to the tubular microconveyor, but formed as a series of evenly spaced conductive lines on the surface of a semiconductor die is also described. Other aspect of the invention are directed to using the microconveyors in conjunction with an electrostatic accelerator to "sort" or select particles by directing them through specific apertures into associated bins or reservoirs.

9 Claims, 8 Drawing Sheets

MICROMACHINED CONVEYOR DEVICES

TECHNICAL FIELD OF THE INVENTION

The invention relates to micromachined devices and, more particularly, to techniques for creating mechanically useful devices using semiconductor or other materials and fabrication techniques.

BACKGROUND OF THE INVENTION

"Micromachining" as the term is used herein, refers to a field of endeavor where extremely small (microscopic) mechanical devices are fabricated, often using semiconductor processing techniques, as on silicon dies. The techniques employed in the fabrication of these devices include those used to fabricate traditional semiconductor electronic devices—namely, deposition, doping, implantation, photolithography, etching, et cetera. However, the technologies employed to fabricate these devices has expanded from traditional semiconductor fabrication processes to more "conventional" techniques of cutting and grinding.

In some cases, mechanical and (as well as) electrical elements are fabricated on silicon to form a device such as a micromotor. In many cases, forming microscopic versions of mechanical devices poses some difficult problems in micromachining analogous devices on silicon. For example, making a rotor turn on a bearing is probably the most difficult task for a would-be micromechanic, since a theoretical understanding of friction on the microscale is lagging behind classical notions of friction on larger, more familiar scales.

There are already a number of mechanical "primitives" (for example wheels and levers) for micromachined devices. Among these are gears, rotors, levers and the like, useful in fabricating micromotors, microscopic tweezers, microprobes, micro-positioning arms, micro cantilevers, micro valves, micro bearings and bushings, cilia-like curling actuators, membranes, expanding/contracting parallelogram devices, and the like.

By and large, most micromachined devices are based on primitives that operate in the plane of the silicon substrate. Recently, however, primitives are being developed whose motion is perpendicular to the substrate. For example, actuators are being developed that curl up off the surface of a silicon die, and relax back onto the surface, akin to the motion of cilia. A purely upright element would evidently be useful for implementing grasping functions, akin to the movement of human fingers.

Generally, the field of micromachining is dominated by efforts to fabricate microscopic analogues of macroscopic devices and primitives in the medium of silicon. To some extent, this would appear to be antithetical to the generally accepted goal of replacing mechanical elements with electronic elements having fewer (perhaps none) moving parts.

There remains a need for additional micromachined devices, and primitives for such devices, which will expand the useful horizons of and applications for micromachining.

DISCLOSURE OF THE INVENTION

In the context of the present invention, a micromachined device includes any structure formed on a substrate (typically silicon, or similar material, but including any other compound, alloy or material) that can perform work (in the mechanical sense of the term "work"), such as moving or exerting a force on a mass.

It is an object of the present invention to provide an improved micromachined device.

It is another object of the invention to provide an improved technique for making micromachined devices.

According to a preferred embodiment of the invention, a microconveyor is fabricated on a silicon die, and has the ability to move (propel) substances (material), such as particles, from one point to another.

Generally, in the embodiments that follow a plurality of evenly spaced conductive elements are energized with a set of driving waveforms in staggered phase to create an electrostatic travelling wave through a tube or across a surface. Charged particles (or suitable fluid or gas molecules, hereinafter referred to as "particles") can be propelled along the wave by electrostatic attraction/repulsion such that they are transported through the tube or across the surface.

In one embodiment of the micromachined conveyor of the present invention, a tube is formed of an insulating material. Conductors are provided circumferentially (axially-spaced rings) or spirally along the length of the tube. Suitable voltages are applied to the conductors, in suitable phase, so that particles at one end of the tube are conveyed within the tube to the other end of the tube.

According to an aspect of the invention, the tube may be a longitudinal passageway through a micromachined drill bit. This would be useful in microsurgery, wherein the micromachine could locate and drill through blood clots and the like, the debris (particles) being conveyed through the drill bit to the bloodstream or to a receptacle for later disposal (e.g., when the micromachine is removed from the body). Means for imparting a charge to the particles, so that they may be electrostatically propelled is envisioned.

According to another aspect of the invention, instead of conveying particles, a micro-thread could be conveyed through the tube—the micromachine being useful for stitching (e.g., such as in medical suturing).

According to another aspect of the invention, such a micromachined conveyor can be used for "cleaning" the interior or exterior of another micromachined device, by moving or repulsing particles from surfaces.

In another embodiment of the micromachined conveyor of the present invention, a planar substrate has a series of spaced-apart electrodes extending along a dimension thereof. In this manner, particles can be conveyed along a surface.

According to an aspect of the invention, a micromachined conveyor is useful for movement of "worked parts" (micromachined workpieces) along a surface.

According to an aspect of the invention, a micromachined conveyor is useful for moving particles into a reservoir, which can provide an actuator function (similar to blowing up a balloon).

In another embodiment of the micromachined conveyor of the present invention, a planar substrate has a layer of insulating material, conducting material on one side of the insulating layer and conducting material on the other side of the insulating layer. One or more apertures are formed through the substrate. By appropriate application of voltages to the conducting layers, a particle or fluid can be caused to move through the aperture.

According to an aspect of the invention, such a micromachined conveyor can function as a medication delivery microsystem and/or as a time delayed chemical or catalyst delivery system for industrial chemical applications. The delivery of such "active" elements to another location would provide for a virtually unlimited number of application, including time-delayed destruction or activation of another element or component.

According to an aspect of the invention, such a micromachined conveyor can function in cooperation with an array of controllable apertures. By segmenting one of the conductive layers, particles from a supply on one side of the substrate can be caused to 'eject' through selected apertures. Applications of such a micromachined conveyor would include: reservoir buildup for weighted decision making or statistical (operations research) applications, selective location of chemical/electrical/physical material injection or addition.

In another embodiment of the invention, the micromachined conveyor serves the function of a diaphragm.

In another embodiment of the invention, the micromachined conveyor fills flexible tube-shaped reservoirs which are perpendicular to the surface of the silicon substrate, and upon pressurizing (by conveying a medium into) and depressurizing (by conveying a medium out of) the tube-shaped reservoirs, the tube-shaped reservoirs can be caused to flex. With one such reservoir acting against a stationary element, or with two such reservoirs disposed in opposition to each other, a grasping function can be implemented on a microscopic scale.

According to a feature of the invention, two or more materials can be conveyed, without mixing, and deposited into two or more respective receptacles (bins), or they can be mixed in a single bin.

Other objects, features and advantages of the invention will become evident in light of the following description thereof.

DETAILED DESCRIPTION OF THE INVENTION

According to the invention, various types of micromachined conveyors and devices incorporating such micromachined conveyors can be formed using (traditionally semiconductor) fabrication techniques for forming the various mechanical and electrical structures associated therewith. It will be readily appreciated by those of ordinary skill in the art that numerous processing techniques are available for forming structures out of semiconductor materials (e.g., silicon, oxidized silicon, and doped silicon) as well as techniques for depositing and patterning metals and other conductors within and around those structures. For example, tube-like "vias" or voids are commonly developed in integrated circuit semiconductor fabrication processes, as well as selective doping or addition of conductive, insulating and semiconductor materials in preselected patterns. Such processes, and others, are considered suitable for construction of the present invention. In general, the present inventive micromachined conveyors propel solid particles (or fluid or gaseous matter) by making use of a traveling electrostatic field, based on the principle of electrostatic attraction/repulsion to propel the particles.

Figure 1A:
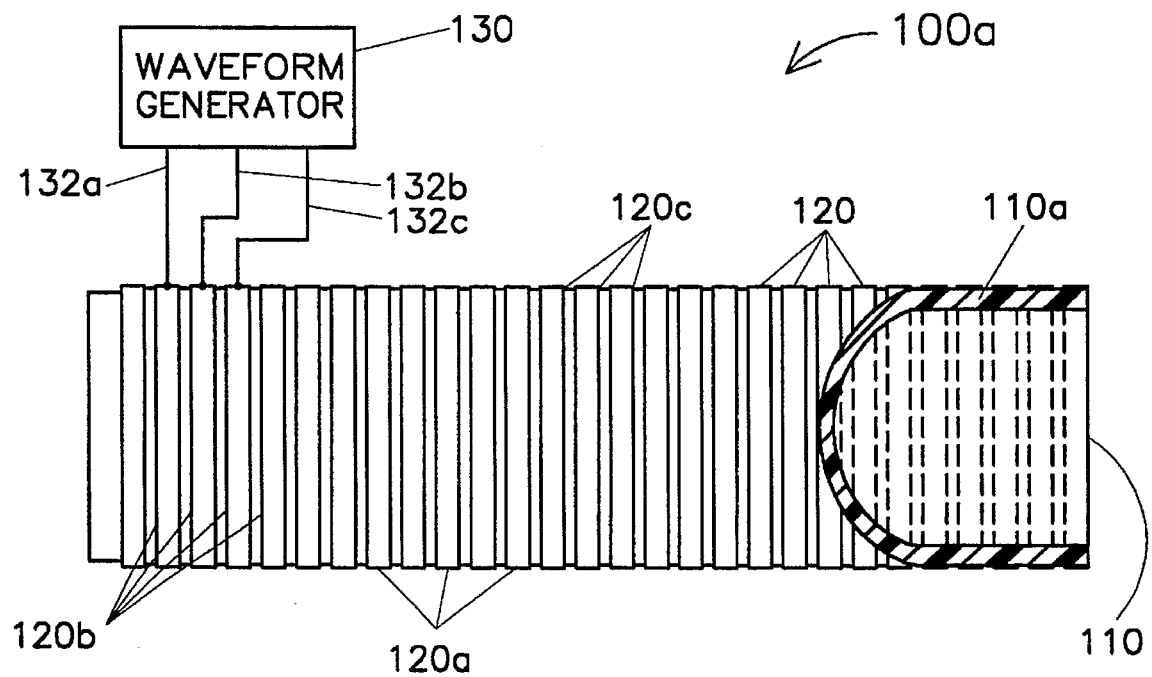
FIG. 1a is a cutaway view of a tubular micromachined conveyor, according to the present invention.

FIG. 1a is a cutaway view of a tubular micromachined conveyor 100a. The conveyor is formed from a tube 110 of an insulating material (e.g., silicon dioxide) around which a plurality of ring-like conductors 120 (e.g., metal or semiconductor material in an active state) are circumferentially disposed. The conductors may be evenly spaced along the length of the tube 110 (or may be spaced irregularly or in patterns of regularity for different purposes). In the Figure, a cutaway portion 110a (for illustrative purposes only) is shown exposing the interior of the tube 110. A waveform generator provides a plurality (in this case, three, but more or less can be appropriate) of driving voltages on a like plurality of lines 132a, 132b, and 132c to selected ones of the ring-like conductors 120. The voltages are cyclic in nature and are offset from one another in phase. For example, a sinusoidal voltage waveform is provided on a first line 132a at a reference phase of 0°. A second sinusoidal voltage waveform is provided on a second line 132b advanced in phase 120° relative to the voltage waveform on the first line 132a. A third sinusoidal voltage waveform is provided on a third line 132c advanced in phase 240° relative to the waveform on the first line 132a. Preferably, the number of waveforms generated by the waveform generator is greater than or equal to three (the number of separate conductor sets), and the waveforms are spaced at even phase intervals about one full cycle (i.e., four sinusoidal waveforms could be provided at 90° intervals, five waveforms at 72° etc.). The waveforms need not necessarily be sinusoidal. The waveforms can be square waves, pulse waves, triangular waves, etc..

Figure 1B:
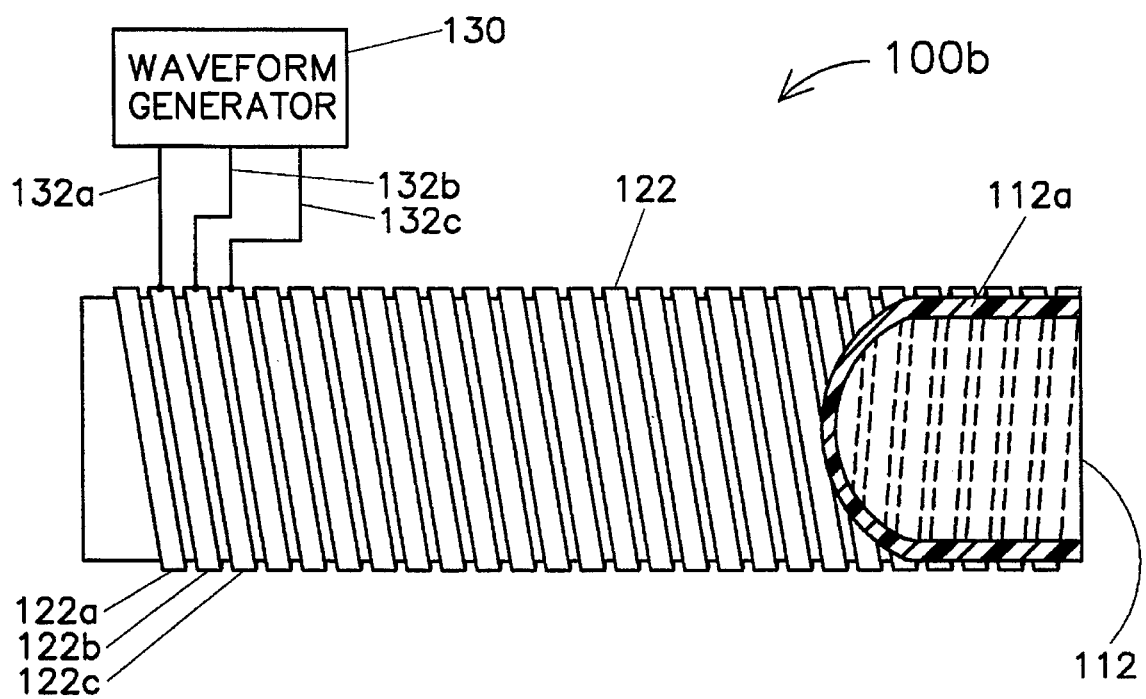
FIG. 1b is a cutaway view of another embodiment of a tubular micromachined conveyor, according to the present invention.

The ring-like conductors 120 are organized into "n" interleaved groups corresponding to the number "n" of voltage waveforms generated by the waveform generator—in this example, three. Preferably, the ring-like conductors 120 in each group are spaced "n" conductors apart from one another along the length of the tube 110 and interleaved such that the voltage waveform provided to each successive conductor 120 along the length of the tube 110 is advanced in phase relative to the waveform provided to the immediate previous conductor. In this manner, a "travelling wave" of voltages is provided (similar to a "marquee" sign effect) along the length of the tube. Each voltage waveform on each ring-like conductor 120 creates an electrostatic field, and the cumulative effect of the electrostatic fields provided by all of the ring-like conductors is a travelling field moving in one direction along the length of the tube 110. Any particle having an electrostatic charge (which one of ordinary skill in the art will realize can be deliberately imparted thereto) which enters the tube 110 (e.g., at the left end as depicted in FIG. 1*b*) will be propelled through the tube 110 by the travelling wave. One of ordinary skill in the art will appreciate that the conveyor 100*a* can also be used to propel gas or liquid molecules (e.g., gas ions) through the tube 110. One of ordinary skill in the art will also immediately recognize that reversal of the phase relationships between the voltage waveforms will cause the microconveyor 100*a* to operate in the opposite direction.

In FIG. 1*a*, the number "n" (of phases, and of conductors in a group) is three. A first plurality of conductors 120*a* (three indicated) is formed of conductors spaced apart from one another in threes (i.e., with two intervening other conductors) along the length of the tube 110. A second plurality of conductors 120*b* (three indicated) and a third group of conductors 120*c* (three indicated) are interleaved with the first group 120*a* in a repeating pattern as shown in the Figure. The first line 132*a* carrying the first waveform (sinusoid at 0°) is connected to each conductor 120 in the first group 120*a*, the second line 132*b* carrying the second waveform (sinusoid at 120° advance) is connected to each conductor 120 in the second group 120*b*, and the third line 132*c* carrying the third waveform (sinusoid at 240° advance) is connected to each conductor 120 in the third group 120*c*. (Only one connection is shown for each line 132*a,b,c* in order to reduce illustrative clutter. The other connections are presumed to have been correctly made and will be immediately understood by one of ordinary skill in the art.)

FIG. 1*b* is a cutaway view of another embodiment of a tubular micromachined conveyor 100*b* formed from a tube 112 of insulating material, similar to the arrangement shown in FIG. 1*a*, but having a helical (spiral) pattern of conductors 122 about the exterior of the tube 112, rather than ring-shaped conductors (compare 120, FIG. 1*a*). The conductors 122 are formed in a multiple helix (e.g., double helix, triple helix, quadruple helix, etc.). Preferably, the number of spirally-formed conductors is three or greater. For example, in the embodiment shown in FIG. 1*b*, the conductors 122 are provided as a set of three interleaved, evenly-spaced, spirally formed conductors 122*a*, 122*b* and 122*c*. Because of the spiral (helical) formation of the conductors 122*a*, 122*b*, and 122*c*, each travels a spiral path along the length of the tube 112. Each conductor (122*a*, 122*b* or 122*c*) is offset from the next by a pre-selected distance. The waveform generator 130 (described hereinabove with respect to FIG. 1*a*) is connected such that each line 132*a*, 132*b* and 132*c* connects to a respective spiral conductor 122*a*, 122*b* and 122*c*. The phase-offset waveforms produced by the waveform generator, when applied to the spiral conductors 122*a*, 122*b* and 122*c* produces a travelling wave effect similar to that described hereinabove with respect to FIG. 1*a*, which can be employed in much the same manner to convey particles (or fluid, or gas) through (from one end to the other end of) the tube 112.

Alternatively, the conductors (e.g., 120 or 122) may be placed on the interior of the tube (e.g., 110 or 112) with or without a covering or partially covering interior material, or fully or partially embedded in the tube. Preferably, the interior of the tube should be smooth so as not to trap or catch or inhibit materials traveling through the tube (except where such may be desired, e.g., see description with regards to FIGS. 6*a*, 6*b* and 6*c*.

Figure 2A:
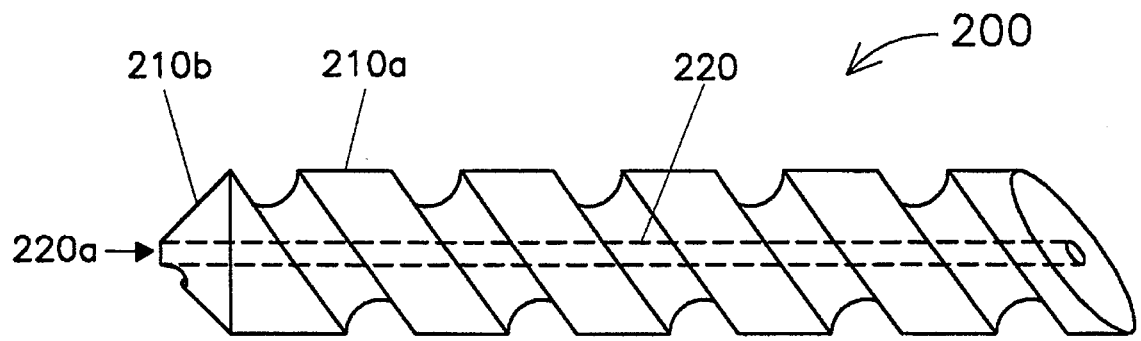
FIG. 2a is a view of a micromachined drill bit having an integral micromachined conveyor, according to the present invention.

FIG. 2*a* is a view of a micromachined drill bit 200, having an integral tubular micromachined conveyor 220 (e.g., of the types described with respect to FIGS. 1*a* and 1*b*). One of ordinary skill in the art will realize that the "spiral" flute pattern along the shaft 210*a* of the drill bit and the shape of the tip 210*b* of the drill bit are merely exemplary. The illustrated shaft and tip shapes are reminiscent of standard "twist" drills, but are not essential to the function of the drill. It should be understood that industrial and medical drills have numerous different tip and shaft shapes suited to specific purposes. It is within the spirit and scope of the present invention that any suitable shaft and/or tip shape be employed. It should also be recognized that the drill bit 200 can be formed in a simple "needle-like" shape with a smooth shaft and pointed tip.

An opening 220*a* of the tubular micromachined conveyor 220 is positioned such that debris resulting from use of the drill bit will enter the opening 220*a*. The tubular micromachined conveyor is similar to those shown in FIGS. 1*a* and 1*b* and is operable to convey the debris through the drill bit 200 along the length of the shaft 210*a*, to a remote location (not shown) for storage or disposal.

Figure 2B:
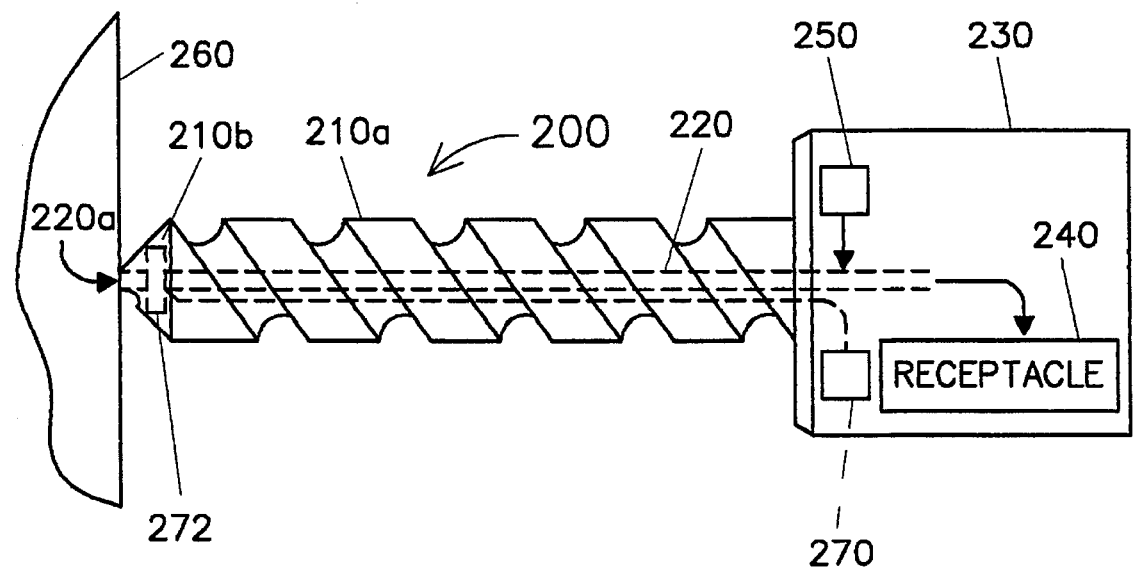
FIG. 2b is a view of a micromachined drill bit and associated apparatus, according to the present invention.

FIG. 2*b* shows the micromachined drill bit 200 of FIG. 2*a* employed to drill through an object 260. The drill bit 200 is attached to a means 230 for actuating (e.g., rotating) the drill bit, such as a micromachined motor. The means for actuating 230 can be adapted, depending upon the form of the drill bit 200, to twist the drill bit 200 about its longitudinal axis, to apply a longitudinal vibration or impulsive force to the drill bit 200, and/or to advance the drill bit 200 into the object (e.g., workpiece) 260. A waveform generator 250 (similar to that shown as 130 in FIGS. 1*a* and 1*b*) is used to apply driving voltage waveforms to the tubular conveyor 220 within the drill bit. As the drill bit 200 operates, debris from the object 260 enters the opening 220*a* of the tubular conveyor 220, causing it to be transported through the drill bit to a receptacle 240 (or alternatively, out of the device altogether). The receptacle 240 can later be emptied of the debris. A charge generator 270 can be employed to impart an electrostatic charge to the particles of debris via an electrode 272 at the tip of the drill bit. It will readily be appreciated by one of ordinary skill in the art that the charge generator 270 and/or the waveform generator 250 can be located either within or without the means for actuating 230, as can the receptacle 240. Preferably, all of the elements shown within the means for actuating are formed on a single silicon die.

The drill bit 200 would be useful in microsurgery, for example, in apparatus for locating and "drilling through" (or piercing or puncturing) blood clots and the like, the debris (particles) being conveyed through the drill bit to the bloodstream (in the absence of a receptacle) or to a receptacle for later disposal (e.g., when the micromachine is removed from the body).

Figure 3A:
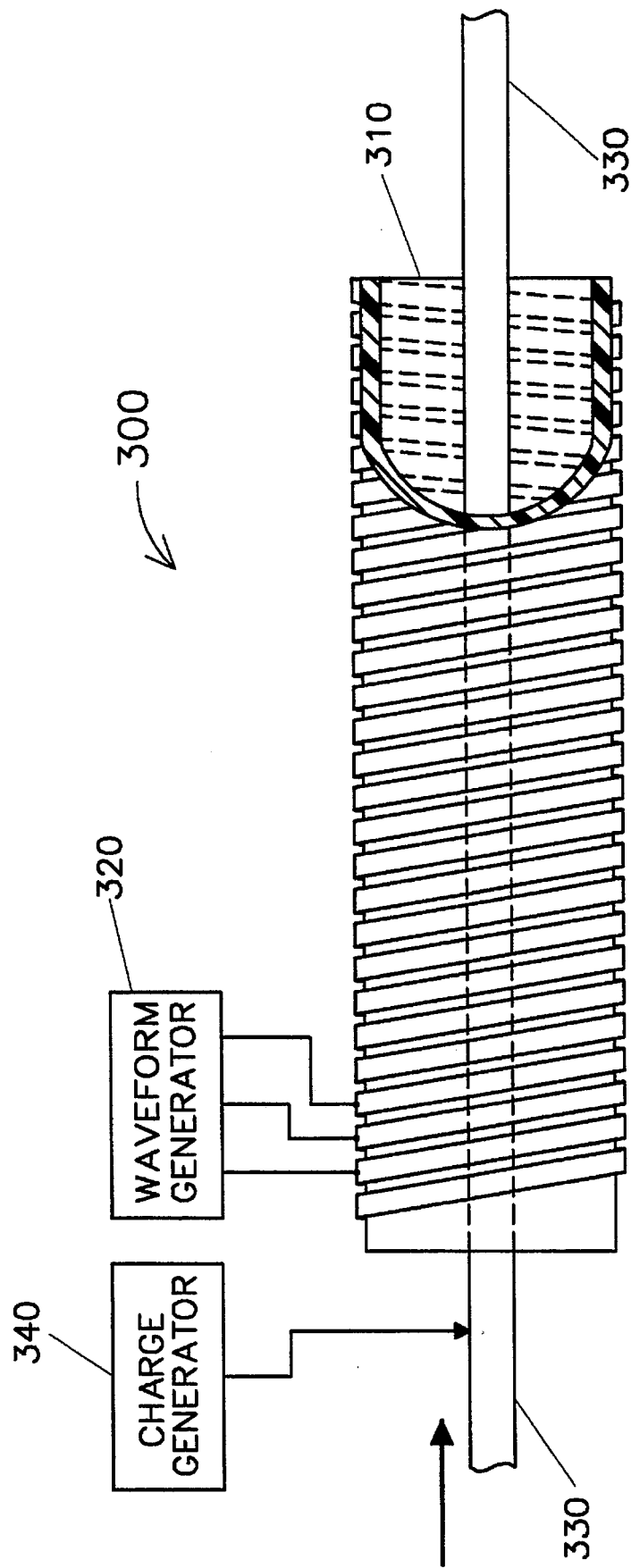
FIG. 3a is a cutaway view of a micromachined conveyor being used to propel a micro-thread, according to the present invention.

FIG. 3a is a cutaway view of a tubular micromachined conveyor 310 being employed in apparatus 300 to propel a microthread 330, according to the invention. A charge generator 340 applies electrical charges to the micro-thread 330 (via a suitable electrode arrangement, not shown). A waveform generator 320 generates a driving electrostatic travelling wave in the (tube-shaped) conveyor 310 (similar to 112, FIG. 1b, for example) to propel the micro-thread 330 through the conveyor 310 by electrostatic attraction/repulsion of the electrostatic charge imparted to the micro-thread 330. Generally, the charge generator is adapted to impart charges at discrete intervals to the thread, as the thread passes the charge generator. In this manner, the thread functions as a carrier for charged particles.

Figure 3B:
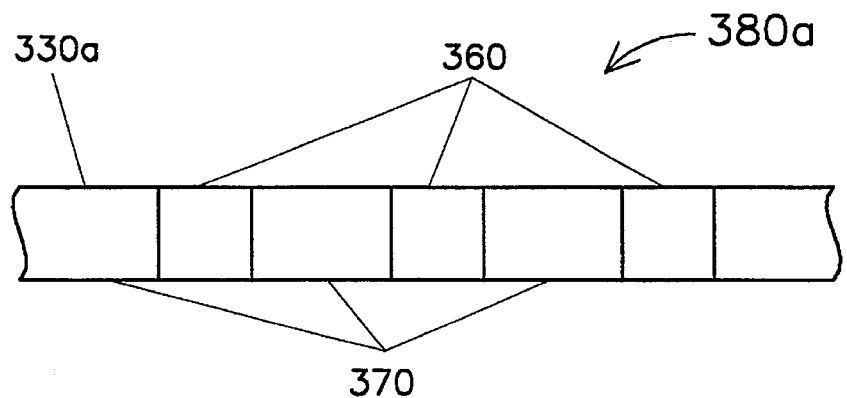
FIG. 3b is a view of one embodiment of a micro-thread suited to application as shown in FIG. 3a, according to the present invention.

FIG. 3b is a view of one embodiment 380a of a microthread 330a suited to application as shown in FIG. 3a, according to the invention. The micro-thread 330a can be formed of a relatively inert material 370 with "slugs" 360 of electrostatically propellable material (i.e., a material will react to the travelling wave in the conveyor) disposed periodically (at intervals) along its length. The slugs 360 act as particles (similar to debris and/or particles described hereinabove with respect to FIGS. 1a, 1b, 2a and 2b) to be propelled through the interior of the tubular conveyor 310, thereby propelling or "feeding" the thread.

Figure 3C:
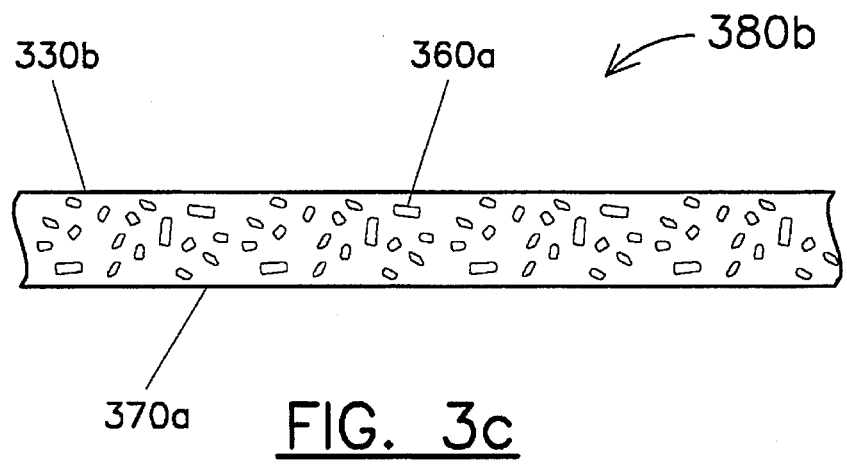
FIG. 3c is a view of another embodiment of a micro-thread suited to application as shown in FIG. 3a, according to the present invention.

FIG. 3c is a view of another embodiment 380b of a microthread 330b, similarly suited to application as shown in FIG. 3a, according to the invention. Like the micro-thread 330a, the microthread 330b can be formed of a relatively inert material 370a, but rather than "slugs" (360), tiny particles 360a of a "propellable" material (similar to the material of the slugs) are embedded within or coated on the inert material 370a of the micro-thread 330b. Like the slugs 360, the particles 360a behave in much the same manner as the debris and/or particles described hereinabove with respect to FIGS. 1a, 1b, 2a and 2b, to be propelled through the interior of the tubular conveyor 310, thereby propelling or "feeding" the thread 330b.

This thread-feeding apparatus (300) of the present invention can be useful in apparatus for micro-stitching (e.g., for feeding a micro-thread in medical microsurgery apparatus for microsuturing).

The foregoing discussion has been directed primarily to tubular conveyors and applications thereof. Attention is now directed to forming micro-planar electrostatic conveyors, for example, on a semiconductor die. Curved and other shapes (other than the tubular and flat shapes extensively disclosed herein) are contemplated as being within the scope of the present invention.

Figure 4:
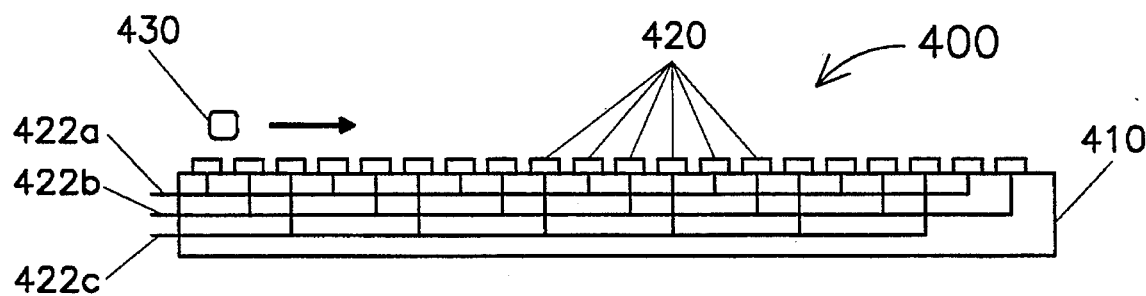
FIG. 4 is a view of a planar silicon microconveyor, according to the present invention.

FIG. 4 is a side view of a planar silicon microconveyor 400 formed on a semiconductor die 410, according to the invention. A plurality of evenly-spaced conductive elements 420 are disposed in a row along the surface of the die 410. The conductive elements 420 are organized in "n" groups as an interleaved repeating pattern of a number of distinct conductive elements (e.g., where "n" is 3, as depicted, a repeating sequence of 1, 2, 3, 1, 2, 3, . . . such that every "$n^{th}$" conductor belongs to the same group). In the Figure, the conductors 420 are organized in three groups, each of which is connected to a respective driving signal conductors 422a, 422b and 422c. (The connections to the conductors 420 in the Figure are shown schematically.) One of ordinary skill in the art will readily appreciate the actual conductive paths to the conductors will normally be embedded within the die 410 or patterned on the surface of the die 410. By applying appropriately phased driving waveforms (similar to those described with respect to FIGS. 1a and 1b) a particle or object 430 can be conveyed electrostatically across the surface of the die 410.

A planar conveyor of the type described with respect to FIG. 4 can be useful, for example, for movement of "worked parts", or debris, (micromachined workpieces) along a surface. Alternatively, such a conveyor may provide a "caterpillar drive" motive force for propelling the die 410 along a surface.

Figure 5A:
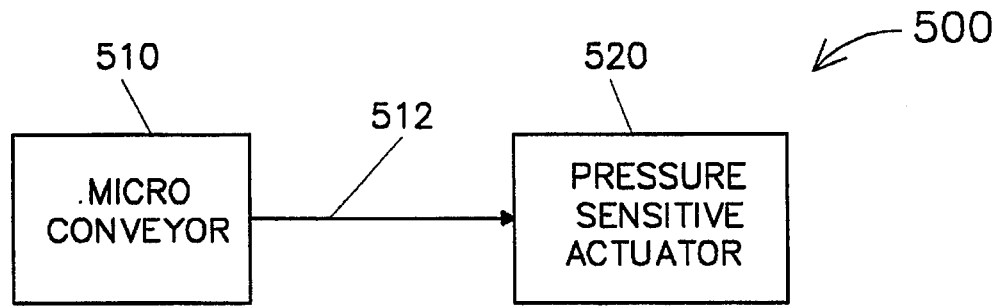
FIG. 5a is a block diagram illustrating the use of a microconveyor to cause mechanical action, according to the present invention.

FIG. 5a is a block diagram illustrating the use of a microconveyor 510, such as those described hereinabove, to cause resulting mechanical action, according to the invention. As discussed hereinabove, a microconveyor (e.g., 510) can be used to propel particles, or suitable fluids or gases. For example, gas ions (charged molecules of gas) can be propelled electrostatically by a microconveyor. Accordingly, since it is possible to move gas molecules from one place to another, it is therefore possible to use a microconveyor to create regions of increased or reduced gas pressure, by conveying gas molecules into or out of an enclosed space. It will be readily appreciated by one of ordinary skill in the art that gas pressure can be used to cause mechanical action, such as, by deflecting a diaphragm, pushing a piston, operating a turbine, or straightening/curling a bourdon tube. By creating microscopic diaphragms, bourdon tubes, turbines and/or pistons and using a microconveyor to propel gas molecules to operate these pressure sensitive devices, microscopic mechanical actions can be performed. In FIG. 5a, this is illustrated in block diagram form whereby the microconveyor 510 is used to propel gas molecules along a path 512 to operate a pressure sensitive actuator 520.

Figure 5B:
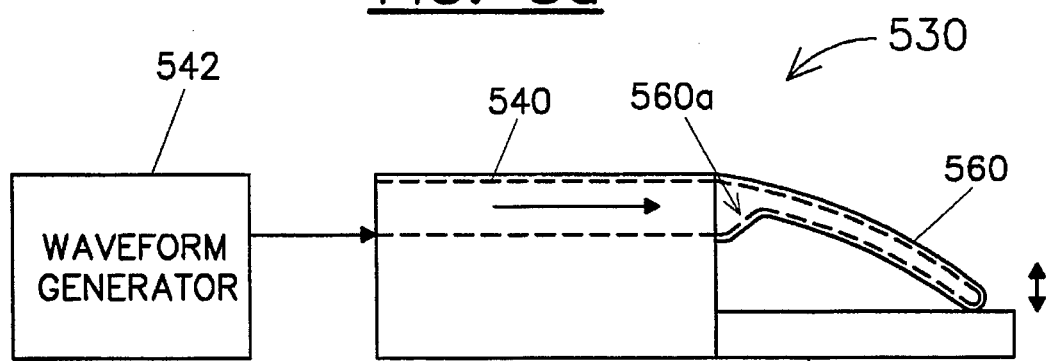
FIG. 5b is a diagram of a micro-machined pressure sensitive actuator, according to the present invention.

FIG. 5b shows an example of such an arrangement 530, whereby a micromachined, flexible tube 560 (e.g., a bourdon tube) is controlled by operation of a microconveyor 540 to cause a grasping action. The pressure sensitive actuator 560 is formed as a hollow, curved arm which rests against a fixed arm 550 (although multiple flexible arms are also envisioned). The microconveyor 540 is operated via a waveform generator 542 to propel gas (or fluid, or particulate) molecules into the interior 560a of the curved, flexible arm 560. The curved arm behaves like a bourdon tube, and tends to straighten with increased pressure, thereby causing the end of the curved arm to raise away from the fixed arm 550. Removal of the driving force of the microconveyor 540 causes the elevated gas pressure to dissipate, thereby causing the curved arm 560 to return to its natural curved state. By reversing the direction of the microconveyor (as discussed hereinabove with respect to FIG. 1a), gas molecules are moved out of the interior 560a of the curved arm 560, lowering the pressure therein. The reduced pressure causes the curved arm to curl, thereby applying a force against the fixed member 550. One of ordinary skill in the art will readily understand that two or more curved arms similar to the arm 560 can be arranged opposing one another and operating in a manner analogous to a pair of pinching fingers.

It will readily be appreciated by one of ordinary skill in the art that the capability of the microconveyor to selectively increase and reduce gas pressure can be used with any of the aforementioned pressure sensitive devices to perform mechanical operations. An advantage of effecting mechanical action with gas pressure (as opposed to a rotating motor) is that the microconveyor is entirely solid state (has no moving parts) and consequently creates little or no friction in its operation. This property can potentially extend the useful life of any apparatus beyond that which would be possible with micro-motors, etc..

Figure 6A:
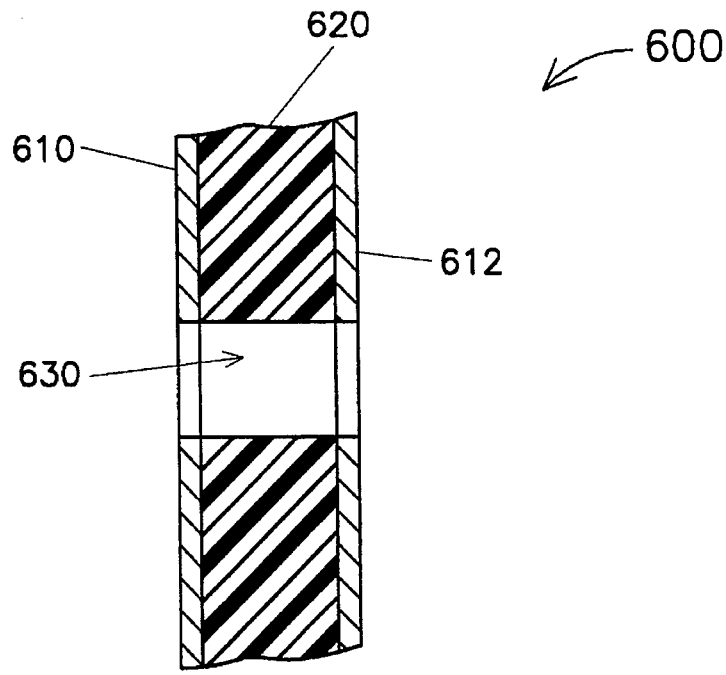
FIG. 6a is a cross-sectional view of apparatus for accelerating a particle through an aperture, according to the present invention.

FIG. 6a is a cross-sectional view of an apparatus 600 for moving a particle through an aperture, according to the invention. A planar insulating substrate 620 is provided with a first conductive layer 610 on one side, and is provided with a second conductive layer 612 on an opposite side. An aperture 630 extends through the insulating substrate 620 and the two conductive layers 610 and 612. Evidently, an electrostatically charged particle near the aperture 630 can be accelerated (caused to move) through the aperture 630 by application of appropriate accelerating potentials to the two conductive layers 610 and 612. The apparatus 600 can be used in conjunction with a microconveyor to propel particles transported towards the aperture 630 through the aperture into, for example, a collecting vessel or reservoir; or forming a collecting vessel or reservoir through an aperture.

Figure 6B:
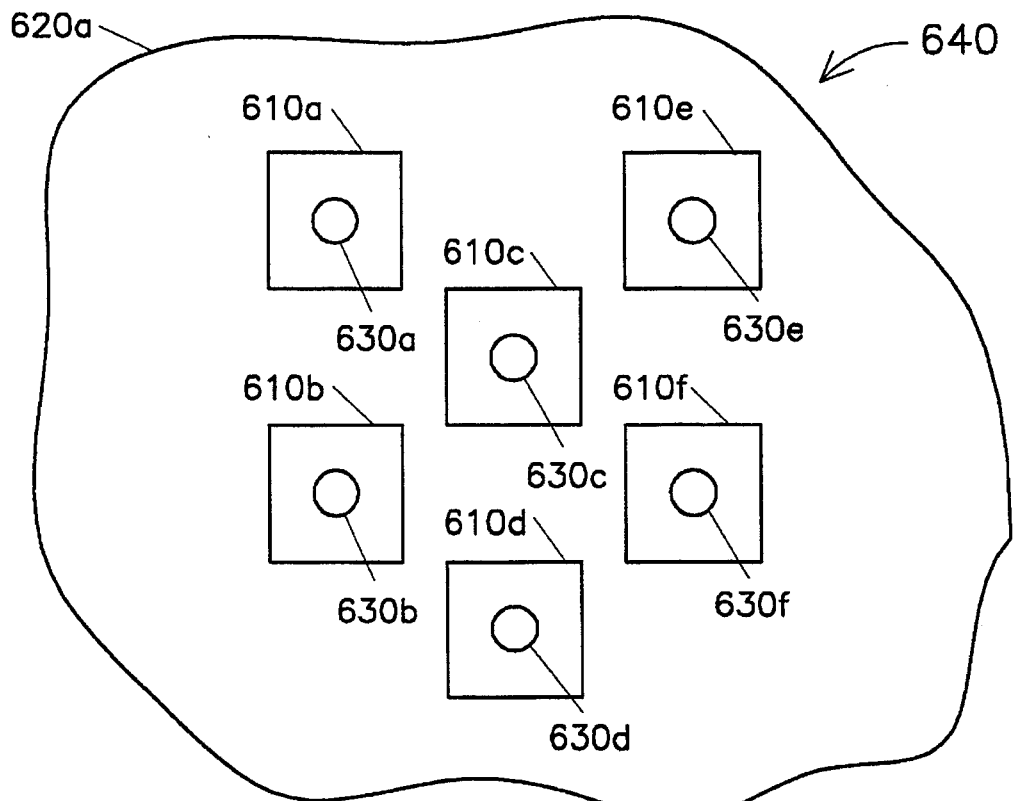
FIG. 6b is a view of a multi-aperture apparatus for accelerating one or more particles through a selected aperture, according to the present invention.

FIG. 6b is a view of a multi-aperture apparatus 640, similar to the apparatus 600 of FIG. 6a, for accelerating one or more particles through a selected aperture. A planar insulating substrate 620a is provided on both (opposite) sides (surfaces) with conductive material (conductive layers, similar to the layers 610 and 612 of FIG. 6a). A plurality of apertures (six shown, 630a, 630b, 630c, 630d, 630e, and 630f) extend through the insulating substrate 620a and the conductive layers. The conductive layer on at least one side, however, is segmented into discrete sections surrounding the various apertures. In the Figure, six discrete areas of conducting material 610a, 610b, 610c, 610d, 610e, and 610f surround apertures 630a, 630b, 630c, 630d, 630e, and 630f, respectively. By applying appropriate accelerating and/or repelling potentials to the various discrete conducting areas (610a-f) an electrostatically charged particle can be caused to be propelled through a particular one of the apertures. For example, an accelerating potential can be applied relative to the aperture 630a while repelling potentials (or no potentials) are applied relative to all of the other apertures (630b-f) to cause particles (including liquids or gas) approaching the multi-aperture apparatus 640 to be propelled only through the aperture 630a (or to propel particles from a reservoir associated only with aperture 630a to be propelled through aperture 630a).

Figure 6C:
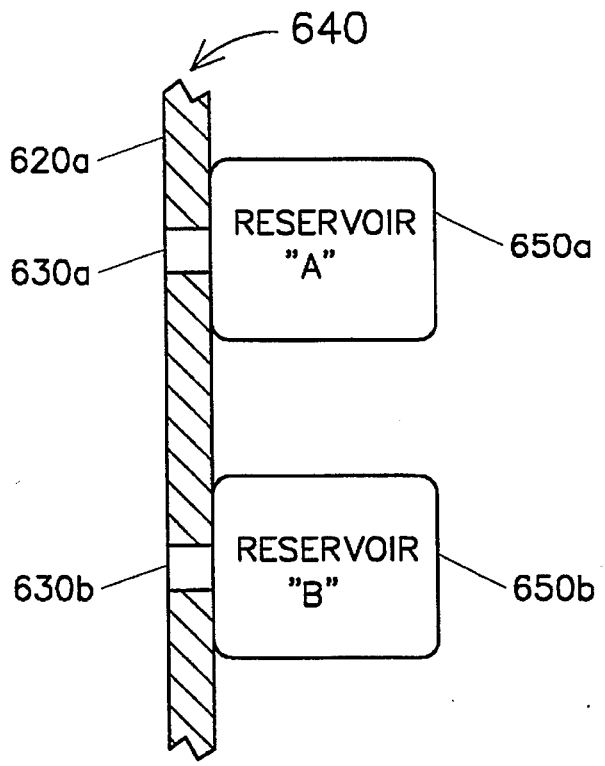
FIG. 6c is a cross-sectional view of apparatus similar to that shown in FIG. 6b, but with a reservoir associated with each aperture for separating and collecting particles accelerated through the various apertures, according to the present invention.

It will readily be appreciated by one of ordinary skill in the art that the inventive apparatus (e.g., 640) can be used to "sort" or "select" particles into separate "bins" or reservoirs. FIG. 6c illustrates this application. One skilled in the art to which this invention pertains will understand that such a sorting mechanism can be employed in conjunction with an appropriate sensing mechanism, to segregate a menagerie of particles into homogeneous groups (for example, by having distinct reservoirs associated with each of the distinct apertures). Alternatively, with various reservoirs associated with apertures 630a-630f, selective mixing of particles (including liquid and gas) can be accomplished (see, e.g., FIG. 7b, described hereinbelow).

FIG. 6c is a cross-sectional view of the apparatus 640 shown in FIG. 6b, but with a reservoir associated with each aperture for separating and collecting particles accelerated through the various apertures, according to the invention. A first reservoir 650a ("Reservoir "A") is provided to capture and collect all particles which pass (i.e., which are caused to be transported, from left to right, for a collection reservoir and from right to left as a source reservoir, as depicted) through the aperture 630a. A second reservoir 650b ("Reservoir "B") is provided to capture and collect all particles which pass through the aperture 630b. (Other reservoirs corresponding to the other apertures 630c-f are not shown, but can be similarly provided.)

Alternatively, the apparatus 640 can be operated in reverse such that each of the reservoirs initially contain particles of a different type. By appropriate application of accelerating voltage (potential) particles can be selectively expelled from one or more of the reservoirs through the apertures associated therewith. In this manner, particles of different materials can be brought together with one another in a controlled manner, such as for assembling molecules or medications, on a microscopic scale.

Other (e.g., additional) combinations of the techniques discussed above may become apparent to one having skill in the art to which this invention most nearly pertains, and such other combinations are deemed to be within the spirit and scope of the present invention.

Figure 7A:
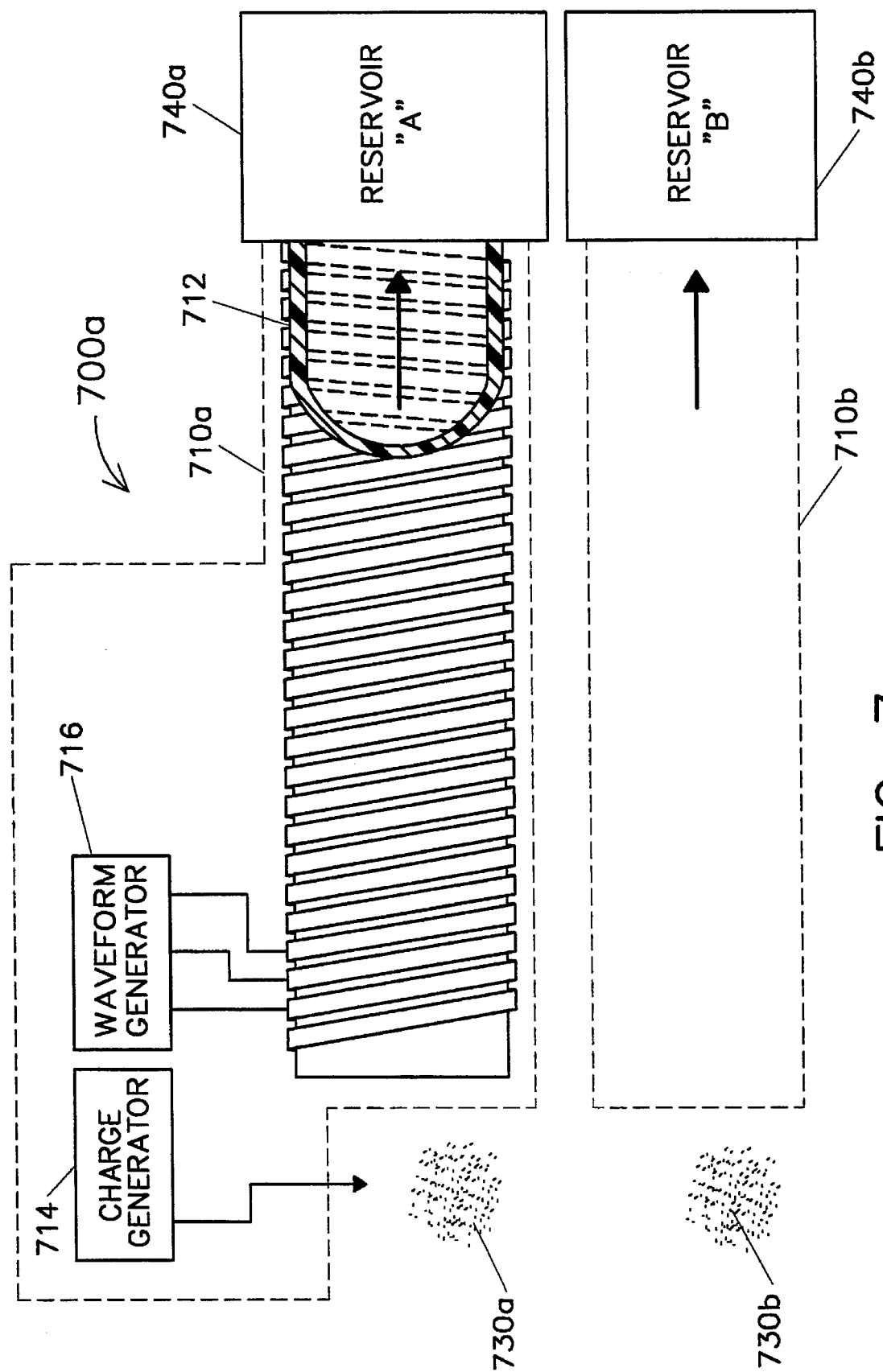
FIG. 7a is a view of apparatus for conveying several (two shown, could be three or more) materials to a corresponding number of bins (reservoirs), according to the present invention.

For example, FIG. 7a, illustrates a multiple conveyor apparatus 700a wherein two materials 730a and 730b are conveyed separately through two separate conveyors 710a and 710b to two separate reservoirs 740a ("Reservoir A") and 740b ("Reservoir B"). The conveyors 710a and 710b are of any of the types described hereinabove and may, for example, be fabricated on a common substrate. The conveyor 710a, for example, includes a spirally-wound electrostatic conveyor tube 712, a charge generator 714 for imparting an electrostatic charge to the material 730a to be conveyed, and a waveform generator 716 for creating a travelling electrostatic wave within the tube 712 to transport the material 730a through the tube 712 to the reservoir 740a. Conveyor 710b is suitably essentially identical to the conveyor 710a, and further elements of this conveyor are omitted, for illustrative clarity.

Figure 7B:
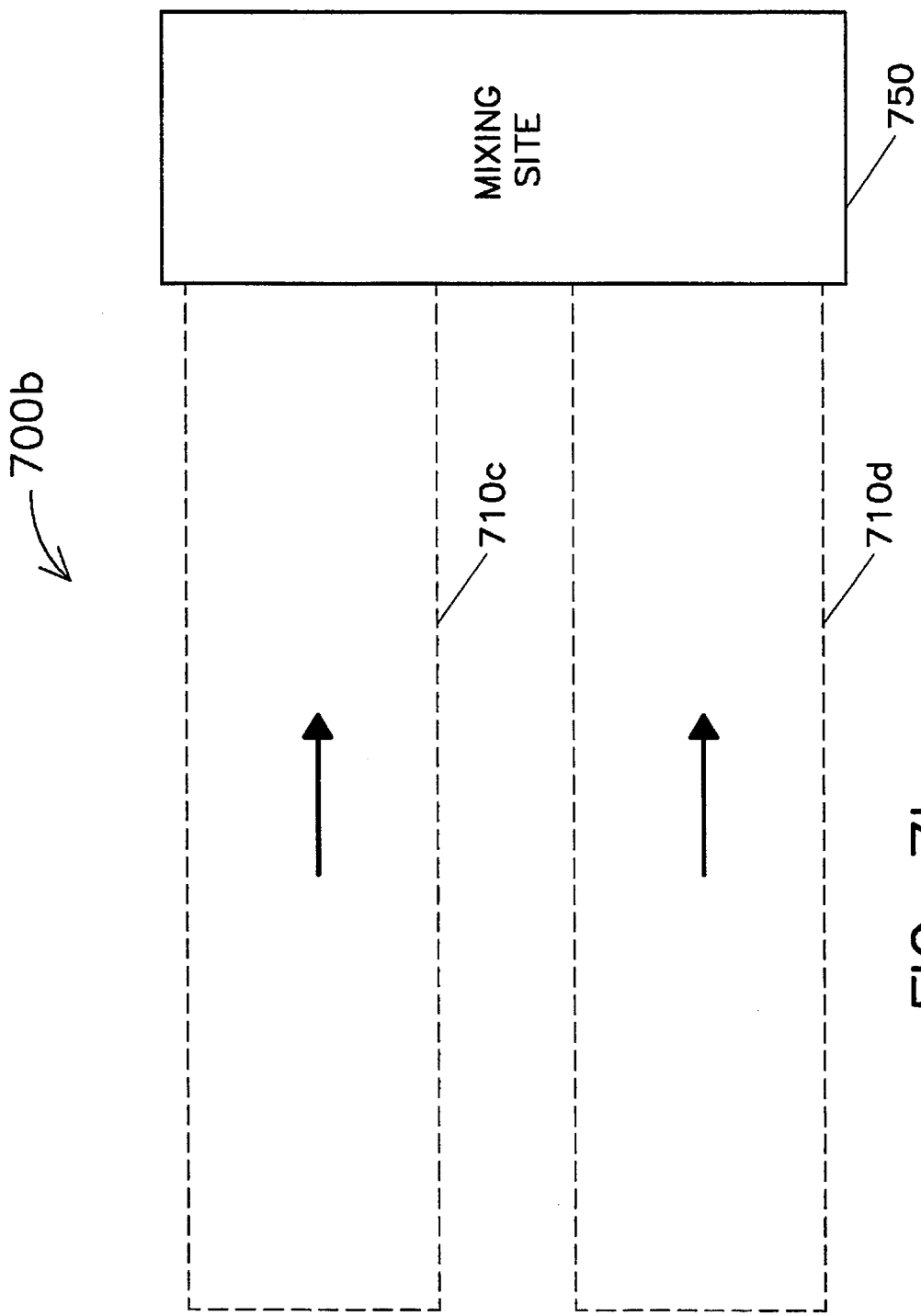
FIG. 7b is a view of apparatus for mixing several (two shown, could be three or more) materials in a bin (reservoir), according to the present invention.

FIG. 7b illustrates a multiple conveyor mixing apparatus 700b, similar to the multiple conveyor apparatus 700a of FIG. 7a which can be fabricated on a single substrate. The mixing apparatus of this embodiment 700b includes two conveyors 710c and 710d for transporting materials 730c and 730d, respectively, to a common mixing site 750 whereat the materials 730c and 730d are combined with one another. The two conveyors 710c and 710d are suitably similar to the conveyor 710a of FIG. 7a, but may be fabricated as any of the exemplary conveyors set forth hereinabove.

One having ordinary skill in the art to which the present invention most nearly pertains will understand that the multiconveyor arrangements of FIGS. 7a and 7b can readily be adapted to conveying three or more materials (including different materials) to separate "bins" or reservoirs, as well as to a common mixing site.

What is claimed is:

1. An apparatus for performing microsurgery, comprising:
    a micromachined drill bit having a longitudinal passageway formed into a tube within the micromachined drill bit, said drill bit having distal and proximate ends;
    a pattern of conductive rings insulated from the tube and disposed along the length of the tube;
    a multiphase waveform generator connected to the conductive rings and applying voltage waveforms to the pattern of conductive rings, in predetermined phase, to create an electrostatic traveling wave along the length of the tube;
    an electrostatic electrode at the proximate end of said drill bit, said electrostatic electrode connected to an electrostatic generator for imparting an electrostatic charge to particles at the proximate end of said drill bit; and means for receiving the particles passing through the tube by the electrostatic traveling wave, said receiving means connected to the distal end of the drill bit.

2. The apparatus of claim 1, wherein the multiphase waveform generator is a three phase waveform generator having a 120 degree phase difference between waveforms.

3. The apparatus of claim 1, wherein the receiving means is a tube adapted to be placed in a patient's body fluid.

4. The apparatus of claim 1, wherein the receiving means is a reservoir.

5. The apparatus of claim 1, further comprising a means for pressuring the receiving means so that fluids do not flow through the tube, wherein only the electrostatically charged particles pass through the tube by the electrostatic traveling wave.

6. Method of performing microsurgery, comprising the steps of:

providing a micromachined drill bit having a longitudinal passageway formed into a tube within the micromachined drill bit;

providing a pattern of conductive rings insulated from the tube and disposed along the length of the tube;

bringing the micromachined drill bit to bear upon an obstruction within a patient's body;

removing at least part of the obstruction with the micromachined drill bit wherein the removed part of the obstruction becomes particles of debris;

applying voltage waveforms to the pattern of conductive rings, in predetermined phase, to create an electrostatic traveling wave alone the length of the tube;

imparting an electrostatic charge to the particles of debris; and conveying the particles of debris through the tube by electrostatic propulsion.

7. A method according to claim 6, further comprising:

conveying the debris particles through the tube into the patient's body fluid.

8. A method according to claim 6, further comprising:

conveying the particles through the tube to a receptacle (reservoir).

9. A method according to claim 6, further comprising a means for pressurizing the receiving means so that fluids do not flow through the tube, wherein only the electrostatically charged particles pass through the tube by the electrostatic traveling wave.

* * * * *